(12) United States Patent
Wakabayashi et al.

(10) Patent No.: US 11,141,194 B2
(45) Date of Patent: Oct. 12, 2021

(54) UTERINE HEMOSTATIC BALLOON UNIT

(71) Applicant: ATOM MEDICAL CORPORATION, Tokyo (JP)

(72) Inventors: Keisuke Wakabayashi, Saitama (JP); Shinichi Kobayashi, Saitama (JP); Tatsuhiko Seki, Saitama (JP); Ichiro Matsubara, Tokyo (JP)

(73) Assignee: ATOM MEDICAL CORPORATION, Tokyo (JP)

( * ) Notice: Subject to any disclaimer, the term of this patent is extended or adjusted under 35 U.S.C. 154(b) by 188 days.

(21) Appl. No.: 16/439,001

(22) Filed: Jun. 12, 2019

(65) Prior Publication Data
US 2019/0388120 A1 Dec. 26, 2019

(30) Foreign Application Priority Data

Jun. 26, 2018 (JP) .............................. JP2018-120607

(51) Int. Cl.
*A61B 17/42* (2006.01)
*A61B 17/12* (2006.01)

(52) U.S. Cl.
CPC .......... *A61B 17/42* (2013.01); *A61B 17/1204* (2013.01); *A61B 17/12136* (2013.01);
(Continued)

(58) Field of Classification Search
CPC .. A61M 29/00; A61M 25/10; A61M 25/1025; A61M 25/104; A61B 17/42;
(Continued)

(56) References Cited

U.S. PATENT DOCUMENTS 5,372,584 A * 12/1994 Zink .................. A61B 10/0291
 604/515
5,624,399 A * 4/1997 Ackerman ............. A61B 17/42
 604/103.03

(Continued)

FOREIGN PATENT DOCUMENTS

EP 0519515 A1 * 12/1992 .......... A61M 25/104
JP 2011-364489 A 2/2011
(Continued)

OTHER PUBLICATIONS

Office Action in Japan Application No. 2018-120607, dated Nov. 16, 2019, 5 pages.
(Continued)

*Primary Examiner* — George J Ulsh
*Assistant Examiner* — Arwa Mostafa
(74) *Attorney, Agent, or Firm* — Crowell & Moring LLP

(57) ABSTRACT

The uterine hemostatic balloon unit includes a tube, a hemostatic balloon, a connector disposed in the tube, and a cap to be detachably attached to a proximal end portion of the tube. The tube has a drain channel for draining uterine blood outward and a water supply channel communicating with the hemostatic balloon. The connector has a drain terminal communicating with the drain channel and disposed in a proximal end portion of the tube, a flexible water supply tube communicating with the water supply channel and extending by being bifurcated outward of the tube, and a water supply terminal communicating with the water supply tube. The cap has an accommodating portion capable of accommodating the water supply terminal along a length direction of the drain terminal. The accommodating portion is open in a direction orthogonal to the length direction of the drain terminal.

20 Claims, 7 Drawing Sheets

(52) U.S. Cl.
CPC .............. *A61B 2017/12004* (2013.01); *A61B 2017/1205* (2013.01); *A61B 2017/4216* (2013.01)

(58) Field of Classification Search
CPC .......... A61B 17/1204; A61B 17/12136; A61B 2017/1205; A61B 2017/4216; A61B 2017/12004; A61B 17/4241; A61B 25/1018; A61B 2025/1061; A61B 2025/1063
See application file for complete search history.

(56) References Cited

U.S. PATENT DOCUMENTS

| | | | |
|---|---|---|---|
| 6,032,064 A | 2/2000 | Devlin et al. | |
| 8,123,773 B1 * | 2/2012 | Shirley | A61M 25/1002 606/193 |
| 8,292,794 B2 * | 10/2012 | Lubock | A61N 5/1015 600/3 |
| 2003/0060803 A1 * | 3/2003 | McGlinch | A61M 25/002 604/533 |
| 2006/0173486 A1 * | 8/2006 | Burke | A61B 17/12099 606/193 |
| 2007/0167822 A1 | 7/2007 | Webler et al. | |
| 2013/0096604 A1 * | 4/2013 | Hanson | A61M 25/104 606/194 |
| 2016/0250466 A1 | 9/2016 | Boggs, II et al. | |
| 2018/0360494 A1 * | 12/2018 | Melsheimer | A61M 25/0097 |

FOREIGN PATENT DOCUMENTS

| | | | |
|---|---|---|---|
| JP | 2011-512994 A | 4/2011 | |
| JP | 6012428 | 9/2016 | |
| JP | 6012428 B2 | 10/2016 | |
| JP | 2016-221247 A | 12/2016 | |
| WO | WO-0038776 A1 * | 7/2000 | ........ A61M 25/1006 |
| WO | WO-2011053415 A1 * | 5/2011 | ............. A61F 2/958 |

OTHER PUBLICATIONS

Extended European Search Report in Europe Application No. 18864934.7, dated Jun. 1, 2021, 7 pages.

* cited by examiner

UTERINE HEMOSTATIC BALLOON UNIT

RELATED APPLICATIONS

Priority is claimed on Japanese Patent Application No. 2018-120607, filed on Jun. 26, 2018, the content of which is incorporated herein by reference.

BACKGROUND OF THE INVENTION

1. Field of the Invention

The present invention relates to a uterine hemostatic balloon unit that prevents bleeding inside a uterus.

The application claims the benefit of priority to Japanese Patent Application No. 2018-120607 filed Jun. 26, 2018, the contents of which are hereby incorporated by reference in the entirety.

2. Description of the Related Art

In the related art, a hemostatic balloon unit is known as follows. A hemostatic balloon is inserted from a vaginal portion, and is located inside a uterus. Thereafter, the balloon is inflated by injecting air or water into the balloon. In this manner, the hemostatic balloon unit performs compression hemostasis on bleeding. The hemostatic balloon unit has a drain channel for draining uterine blood and a water supply channel for injecting a liquid into the balloon. Normally, in a case where a hemostatic balloon is inserted into the uterus from outside of a body, the hemostatic balloon is inserted into a vagina and located inside the uterus by being pushed. Then, the liquid is injected into the hemostatic balloon via a connector of the water supply channel disposed in an end portion on a side opposite to the hemostatic balloon, and the balloon is inflated. In this manner, the compression hemostasis is performed on a bleeding site.

On the other hand, in a case of a patient subjected to caesarean section, the connector of the hemostatic balloon unit is inserted into the uterus from an incised portion of the patient. The connector is pulled out of the patient's body through the vagina, and the hemostatic balloon is located inside the uterus. For example, the hemostatic balloon unit disclosed in Japanese Patent No. 6012428 is known as the hemostatic balloon unit in which the connector can be exposed outward by inserting the connector into the uterus in advance from the incised portion in this way.

The hemostatic balloon unit disclosed in Japanese Patent Publication No. 6012428 has a hemostatic balloon in a distal end portion of a flexible tube, and is configured to include a hemostatic balloon catheter in which the connector is disposed in a proximal end portion of the tube, and a connector cover to be detachably attached to the proximal end portion of the balloon catheter. The tube internally includes a first passage which is open on a distal end side of the hemostatic balloon and a second passage which communicates with the hemostatic balloon. The connector includes a first terminal which communicates with the first passage and a second terminal which communicates with the second passage and which is bifurcated at a first angle from a root portion of the first terminal. The connector is configured to be bendable by allowing at least one of the root portions of the first terminal and the second terminal to be flexible. The connector cover includes a terminal accommodating portion configured so that the first terminal and the second terminal can be accommodated in a state where the first terminal and the second terminal are bent to form a second angle which is more acute than the first angle. In this manner, the first terminal and the second terminal are inserted into the uterus in a state where the first terminal and the second terminal are combined with each other by the connector cover.

SUMMARY OF THE INVENTION

Problems to be Solved by the Invention

However, according to a configuration disclosed in Japanese Patent No. 6012428, a configuration is adopted in which the first terminal and the second terminal are accommodated in the connector cover. Accordingly, a diameter of the connector cover increases, and the connector is less likely to be inserted into a narrow portion such as a uterine os. If the connector is forcibly inserted the uterine os, there is a risk of damage to a birth canal. In addition, work for respectively accommodating the first terminal and the second terminal in the connector cover is complicated.

The present invention is made in view of these circumstances, and an object thereof is to provide a uterine hemostatic balloon unit that can prevent damage to a birth canal with a more convenient configuration.

Means for Solving the Problem

According to the present invention, there is provided a uterine hemostatic balloon unit including a flexible tube, a hemostatic balloon disposed in a distal end portion of the tube, a connector disposed in the tube, and a cap to be detachably attached to a proximal end portion of the tube. The tube has a drain channel for draining uterine blood outward by being open on a distal end side from the hemostatic balloon, and a water supply channel communicating with the hemostatic balloon. The connector has a drain terminal communicating with the drain channel and disposed in a proximal end portion of the tube, a flexible water supply tube communicating with the water supply channel on a distal end side from the drain terminal and extending by being bifurcated outward of the tube, and a water supply terminal disposed in a proximal end of the water supply tube and communicating with the water supply tube. The cap detachably fits to an opening of the drain terminal and has an accommodating portion capable of accommodating at least a portion of the water supply terminal along a length direction of the drain terminal. The accommodating portion is open in a direction orthogonal to the length direction of the drain terminal.

According to the present invention, the accommodating portion is formed so that the water supply terminal can be accommodated along the length direction of the drain terminal. Accordingly, if the water supply terminal is accommodated in the accommodating portion, in a case where the uterine hemostatic balloon unit is viewed from the connector side, the cap and the water supply terminal are in an overlapped state. That is, the diameter of the connector can be reduced, compared to a case where the drain terminal and the water supply terminal are arrayed in the direction orthogonal to the length direction of the drain terminal. Accordingly, when the cap is inserted from an incised portion of a patient subjected to caesarean section, insertion resistance can be reduced. Therefore, it is possible to prevent damage to a birth canal which is likely to be damaged when the uterine hemostatic balloon unit is inserted from the incised portion of the patient subjected to the caesarean section.

As a preferred aspect of the uterine hemostatic balloon unit according to the present invention, the accommodating portion may have a stopper portion which regulates movement of the water supply terminal in the direction orthogonal to the length direction of the drain terminal, and the stopper portion may have a clamping portion which clamps the water supply tube on the drain terminal side in the accommodating portion, when the water supply terminal is accommodated inside the accommodating portion.

In the above-described aspect, the clamping portion can clamp and hold the water supply tube on the drain terminal side in the accommodating portion. Accordingly, the water supply terminal can be prevented from being detached from the cap when the cap is inserted into the patient's body from the incised portion. Therefore, while the cap is inserted, it is possible to prevent the insertion resistance from increasing due to the water supply terminal detached from the accommodating portion.

As a preferred aspect of the uterine hemostatic balloon unit according to the present invention, the accommodating portion may have a stopper portion which regulates movement of the water supply terminal in the direction orthogonal to the length direction of the drain terminal, and the stopper portion may have a projection which projects from a surface on a side opposite to the drain terminal side in the accommodating portion so as to be fitted into an opening of the water supply terminal, when the water supply terminal is accommodated inside the accommodating portion.

In the above-described aspect, the opening of the water supply terminal is fitted to the projection inside the accommodating portion. Accordingly, it is possible to further prevent the water supply terminal from being detached from the cap when the cap is inserted.

As a preferred aspect of the uterine hemostatic balloon unit according to the present invention, the accommodating portion may be configured to include a through-hole penetrating the cap.

Here, in a case where the accommodating portion is not configured to include the through-hole, that is, in a case where one end of the accommodating portions is closed and the accommodating portions is open in only one direction, if the water supply terminal is not located in an opening direction of the accommodating portion, it is necessary to rotate the cap until the water supply terminal is disposed in the opening direction of the accommodating portion, when the water supply terminal is accommodated. In addition, when the cap is inserted from the incised portion of the patient subjected to the caesarean section, blood or body fluid of the patient may be accumulated inside the accommodating portion in some cases.

In contrast, in the above-described aspect, the accommodating portion is configured to include the through-hole. Accordingly, even if the water supply terminal is located at any position when the cap is accommodated inside the drain terminal, the water supply terminal can be accommodated inside the accommodating portion without rotating the cap. A possibility that the blood or the body fluid may be accumulated inside the accommodating portion can be reduced.

In the above-described aspect, the uterine hemostatic balloon unit may further include a stylet fixed to a distal end side of the cap and holding a shape of the tube when the stylet is inserted into the tube. When the cap is mounted on the opening of the drain terminal, a distal end of the stylet may be located in a portion from a proximal end portion of the hemostatic balloon to a center of the hemostatic balloon.

Here, if the distal end of the stylet extends to the vicinity of the distal end of the drain channel beyond the center of the hemostatic balloon, there is a risk that the stylet may protrude from the distal end of the drain channel. If the stylet is shorter than the proximal end portion of the hemostatic balloon, in a case where the hemostatic balloon is inserted into a uterus from a vagina, the distal end portion of the tube cannot be supported by the stylet. Consequently, the hemostatic balloon is less likely to be inserted into the uterus.

In contrast, in the above-described aspect, the distal end of the stylet is located within the above-described range. Accordingly, the automatic hemostatic balloon unit can be properly inserted into the uterus, and the uterus can be prevented from being damaged by the stylet.

As a preferred aspect of the uterine hemostatic balloon unit according to the present invention, the stylet may be formed of pure aluminum.

In the above-described aspect, the stylet is formed of the pure aluminum. Accordingly, the stylet can maintain a shape thereof at a bent angle, and is deformed when a strong force is applied thereto. Therefore, operability of the uterine hemostatic balloon unit can be improved.

As a preferred aspect of the uterine hemostatic balloon unit according to the present invention, a metal wire rod may be enclosed on a distal end side of the water supply tube.

In the above-described aspect, the metal wire rod is enclosed on the distal end side of the water supply tube, that is, in the distal end of the hemostatic balloon. Accordingly, for example, a position of the hemostatic balloon inside the uterus can be detected using an ultrasonic echo.

Effects of the Invention

According to the present invention, a more simple configuration can prevent damage to a birth canal when a uterine hemostatic balloon unit is inserted.

DETAILED DESCRIPTION OF THE PREFERRED EMBODIMENTS

Hereinafter, an embodiment of a uterine hemostatic balloon unit according to the present invention will be described with reference to the drawings.

[Schematic Configuration of Uterine Hemostatic Balloon Unit]

Figure 1:
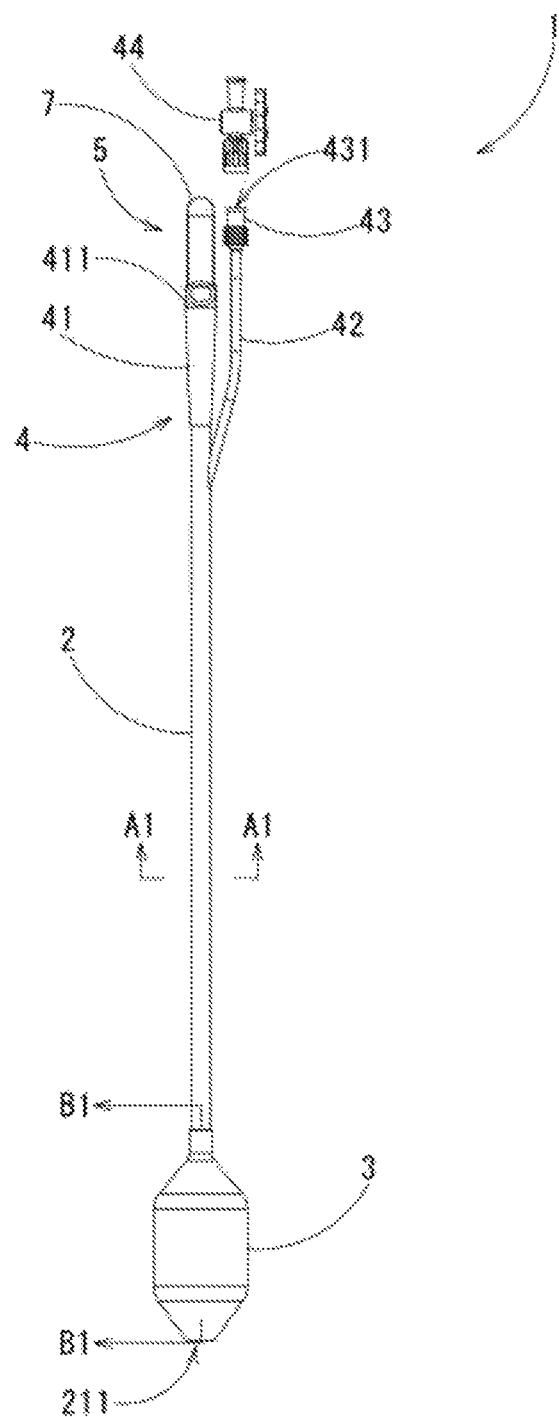
FIG. 1 is a plan view of a uterine hemostatic balloon unit according to an embodiment of the present invention.

As illustrated in FIG. 1, a uterine hemostatic balloon unit (hereinafter, referred to as a balloon unit) 1 according to the present embodiment includes a flexible tube 2, a hemostatic balloon 3 disposed in a distal end portion of the tube 2, a connector 4 disposed in the tube 2, and a cap 7 detachably attached to a proximal end portion of the tube 2.

[Configuration of Tube]

Figure 2:
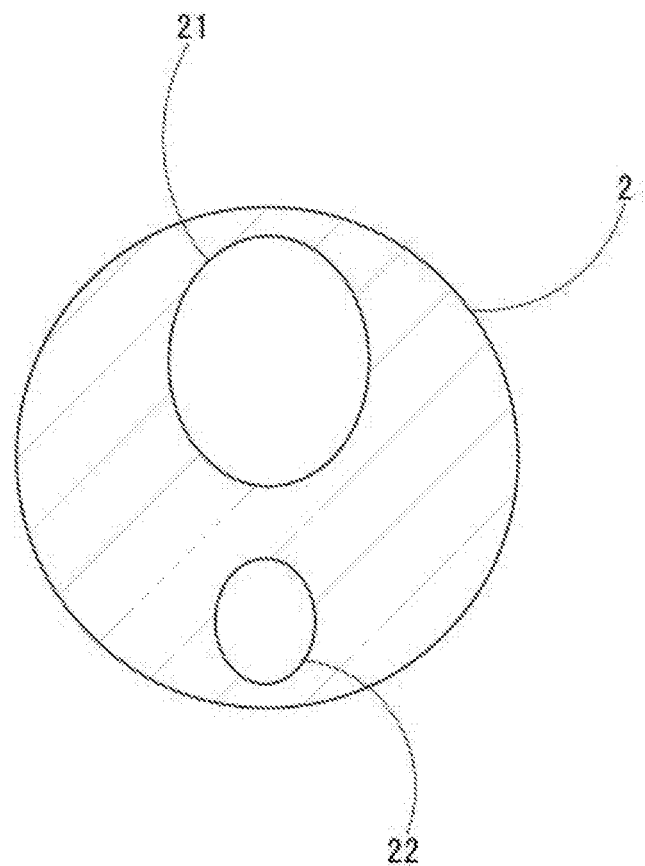
FIG. 2 is a sectional view of a tube which is taken along line A1-A1 in FIG. 1 according to the above-described embodiment.

For example, the tube 2 is formed of a synthetic resin such as polyvinyl chloride, silicone rubber, and thermoplastic elastomer, and is flexible. A line (not illustrated) detectable by using X-rays is applied to the tube 2 along an extending direction of the tube 2. In addition, as illustrated in FIGS. 1 to 3, the tube 2 has a drain channel 21 for draining uterine blood by being open on a distal end side from the hemostatic balloon, and a water supply channel 22 communicating with the hemostatic balloon 3.

Figure 3:
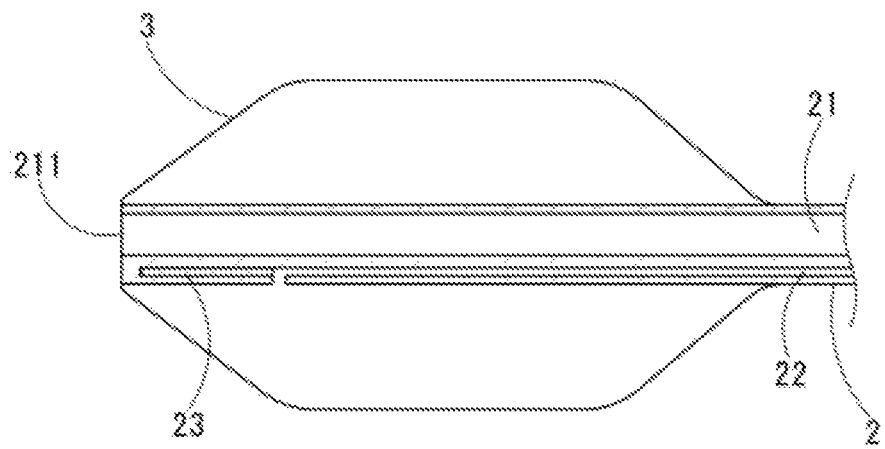
FIG. 3 is a sectional view of the tube which is taken along line B1-B1 in FIG. 1 according to the above-described embodiment.

Out of these, as illustrated in FIG. 3, the drain channel 21 communicates with the tube 2 from a distal end to a proximal end of the tube 2, and a distal end portion thereof has an opening 211 into which the uterine blood flows. On the other hand, the water supply channel 22 communicates with the tube 2 from the vicinity of the distal end to the vicinity of the proximal end of the tube 2. That is, the water supply channel 22 does not lead to either the distal end or the proximal end of the tube 2.

Here, as described above, the line detectable by using the X-rays is applied to the tube 2. Accordingly, the tube 2 can be detected by using the X-rays. However, in a case where there is no X-ray inspection apparatus, even if the tube 2 of the balloon unit 1 is inserted into a uterus, a position of the tube 2 cannot be detected. In order to cope with this situation, according to the present embodiment, as illustrated in FIG. 3, a metal wire rod 23 is enclosed on a distal end side of the water supply channel 22. The wire rod 23 is formed of metal which can be detected by using an ultrasonic echo. Therefore, even in a case where there is no X-ray inspection apparatus, the position of the hemostatic balloon 3 can be easily detected by using the ultrasonic echo.

The metal wire rod 23 is formed of metal which can be detected by using the ultrasonic echo. However, it is preferable that the wire rod 23 is forded of non-ferrous metal which is resistant to rust. It is more preferable that the wire rod 23 is formed of aluminum or stainless steel which has less influence on a living body. In this case, the wire rod 23 may be formed of pure aluminum having the same composition as that of a stylet 6 (to be described later).

[Configuration of Hemostatic Balloon]

For example, the hemostatic balloon 3 is formed of silicone rubber. The hemostatic balloon 3 is inflated by injecting a liquid such as water via the water supply channel 22. For example, a maximum of 500 ml of the liquid can be injected into the hemostatic balloon 3. A size of the hemostatic balloon 3 can be optionally set. For example, the hemostatic balloon 3 may have a size which enables 600 ml of the liquid to be injected.

[Configuration of Connector]

The connector 4 includes a drain terminal 41 communicating with the drain channel 21 and disposed in the proximal end portion of the tube 2, a flexible water supply tube communicating with the water supply channel 22 on the distal end side from the drain terminal 41 and extending by being bifurcated outward of the tube 2, and a water supply terminal 43 disposed in the proximal end of the water supply tube 42 and communicating with the water supply tube 42.

The drain terminal 41 is a flexible tubular member formed of silicone rubber. The drain terminal 41 is formed in a so-called trumpet shape whose diameter gradually increases toward the proximal end side. The drain terminal 41 communicates with the drain channel 21. Accordingly, the uterine blood flowing from the opening 211 is drained through an opening 411 of the drain terminal 41 via the drain channel 21. Although details will be described later, the cap 7 of a stylet unit 5 is mounted on the opening 411 of the drain terminal 41.

For example, the water supply tube 42 is formed of silicone rubber, and is flexible. The distal end of the water supply tube 42 communicates with the water supply channel 22 inside the tube 2, and extends outward from the vicinity of the proximal end portion of the tube 2. The proximal end of the water supply tube 42 has the water supply terminal 43. For example, the water supply terminal 43 is formed rigid polyvinyl chloride (PVC). The water supply terminal 43 is connected to a two-way cock di illustrated in FIG. 1.

A water feeder (not illustrated) such as a syringe is connected to the two-way cock 44. If the liquid is injected from the water feeder via the two-way cock 44, the liquid is supplied into the hemostatic balloon 3 via the water supply terminal 43, the water supply tube 42, and the water supply channel 22. On the other hand, if the two-way cock 44 is unlocked in a state where the liquid is supplied into the hemostatic balloon 3, the liquid contained inside the hemostatic balloon 3 reversely flows, and the hemostatic balloon 3 is deflated.

[Configuration of Stylet Unit]

Figure 4:
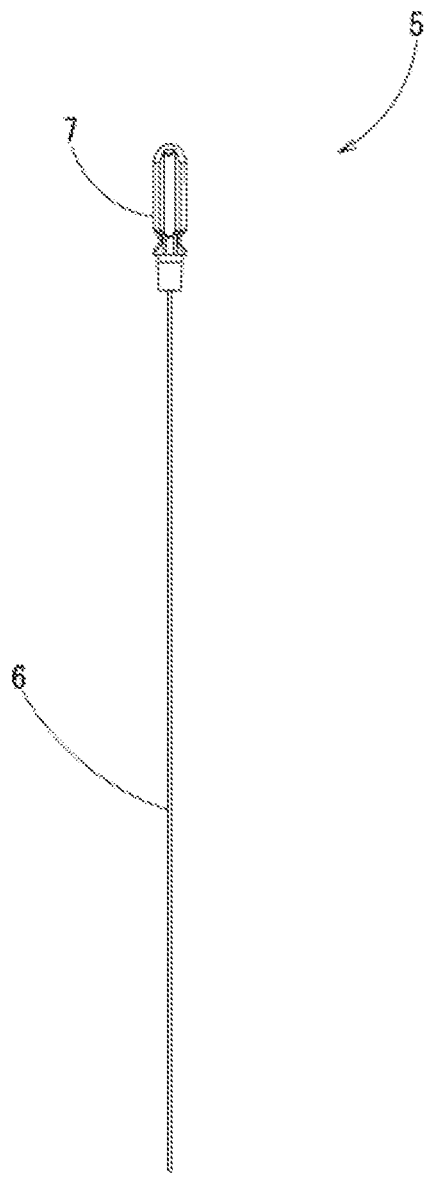
FIG. 4 is a plan view illustrating a stylet of the uterine hemostatic balloon unit according to the above-described embodiment.

As illustrated in FIG. 4, the stylet unit 5 is configured to include a stylet 6 located inside the drain channel 21, and the cap 7 fixed to the proximal end portion of the stylet 6 and detachably fitted into the opening 411 of the drain terminal 41. Out of these, the stylet 6 is configured to include a wire formed of pure aluminum (for example, Al070). In this manner, the stylet 6 can maintain a shape thereof at a bent angle, and is deformed when a strong force is applied thereto.

Here, if the distal end of the stylet 6 extends to the vicinity of the distal end of the drain channel 21 beyond a center of the hemostatic balloon 3, there is a possibility that the stylet 6 may protrude from the distal end of the drain channel 21. If the stylet 6 is shorter than the proximal end portion of the hemostatic balloon 3, in a case where the hemostatic balloon 3 is inserted into the uterus from a vagina, the distal end portion cannot be supported by the stylet 6. Accordingly, the hemostatic balloon 3 is less likely to be inserted into the uterus.

According to the present embodiment, a length of the stylet 6 is set so that the distal end of the stylet 6 is located in a portion from the proximal end of the hemostatic balloon 3 to the center of the hemostatic balloon 3 when the cap 7 is mounted on the opening 411 of the drain terminal 41. In this manner, the uterine hemostatic balloon unit 1 can be properly inserted into a mother's body, thereby preventing the uterus from being damaged by the stylet 6.

[Configuration of Cap]

Figure 5:
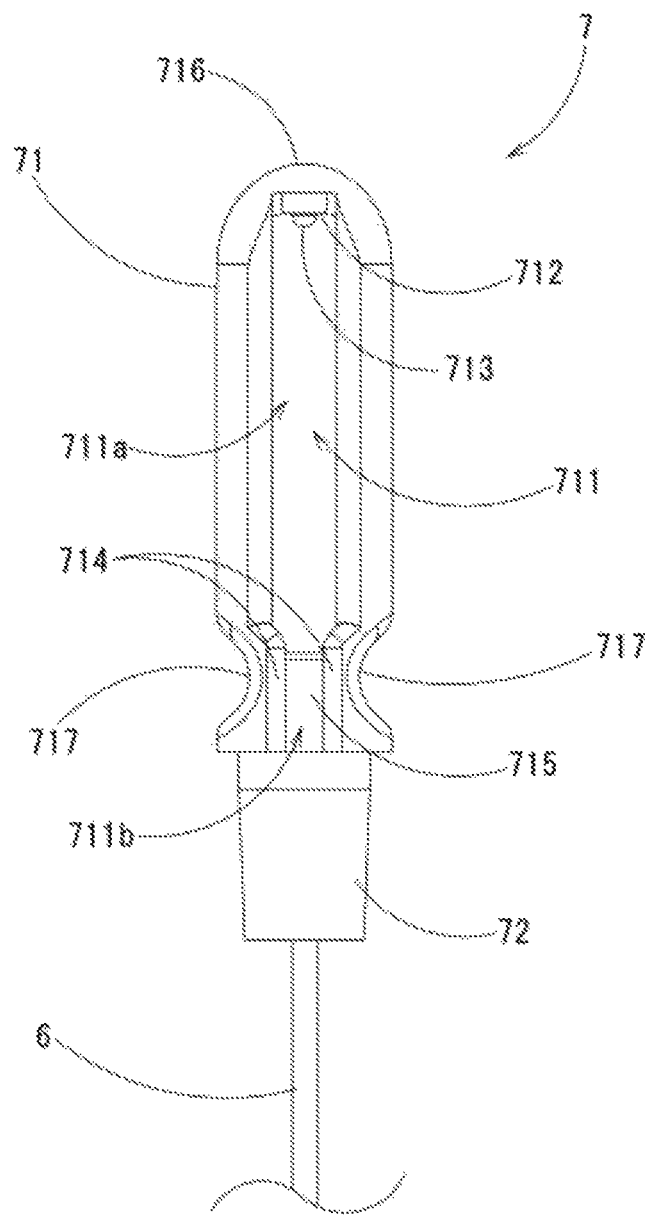
FIG. 5 is an enlarged plan view illustrating a cap of the stylet according to the above-described embodiment.
Figure 6:
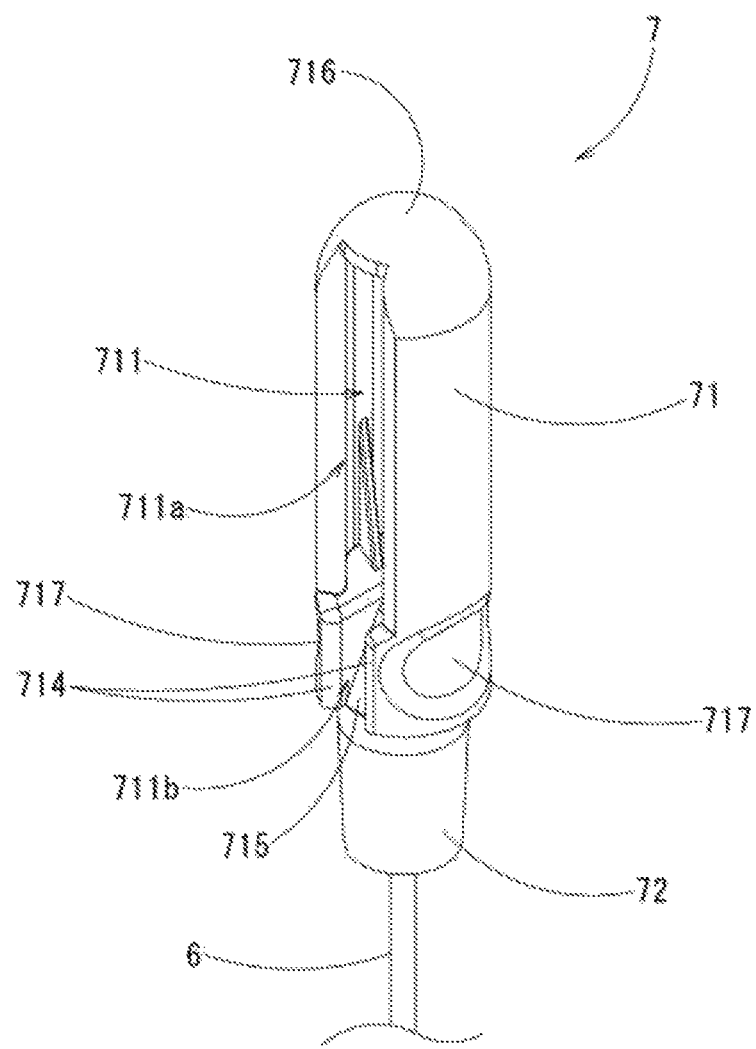
FIG. 6 is an enlarged perspective view illustrating the cap of the stylet according to the above-described embodiment.

For example, the cap 7 is integrally molded using soft polyvinyl chloride or a silicon material. As illustrated in FIGS. 5 and 6, the cap 7 includes a cap main body 71 and a joint portion which is fixed to the distal end portion of the cap main body 71 and which is inserted into and fixed to the opening 411 of the drain terminal 41. Out of these, the joint portion 72 has a shape whose diameter gradually decreases toward the stylet 6, and is formed to be slightly larger than an opening diameter of the drain terminal 41.

The cap 7 is integrally molded. However, without being limited thereto, the cap main body 71 may be formed of the soft poly vinyl chloride or the silicon material. The joint portion 72 may be formed of rigid polyvinyl chloride harder than the soft polyvinyl chloride or the silicon material. In this manner, the cap 7 may be configured so that both of these are joined to each other.

The cap main body 71 has an accommodating portion 711 which can accommodate the water supply terminal 43 and a portion of the water supply tube 42 along a length direction of the drain terminal 41. The accommodating portion 711 is configured to include a through-hole which is open in a direction orthogonal to the length direction of the drain terminal 41. Specifically, the accommodation portion 711 includes a terminal accommodating portion 711a whose diameter is slightly wider than the diameter of the water supply terminal 43 and whose length is longer than the length of the water supply terminal 43, and a water supply tube accommodating portion 711b whose width is narrower than the width of the water supply tube 42, and all of these communicate with each other.

In addition, the accommodating portion 711 includes a stopper portion (projection 713 and clamping portions 714) which regulates movement of the water supply terminal 43 in the direction orthogonal to the length direction of the drain terminal 41. The projection 713 is a portion projecting toward the stylet 6 from a surface 712 on the proximal end side (side opposite to the drain terminal 41) of the through-hole configuring the terminal accommodating portion 711a. When the water supply terminal 43 is accommodated inside the terminal accommodating portion 711a, the projection 713 is fitted into an opening 431 of the water supply terminal 43.

Figure 7:
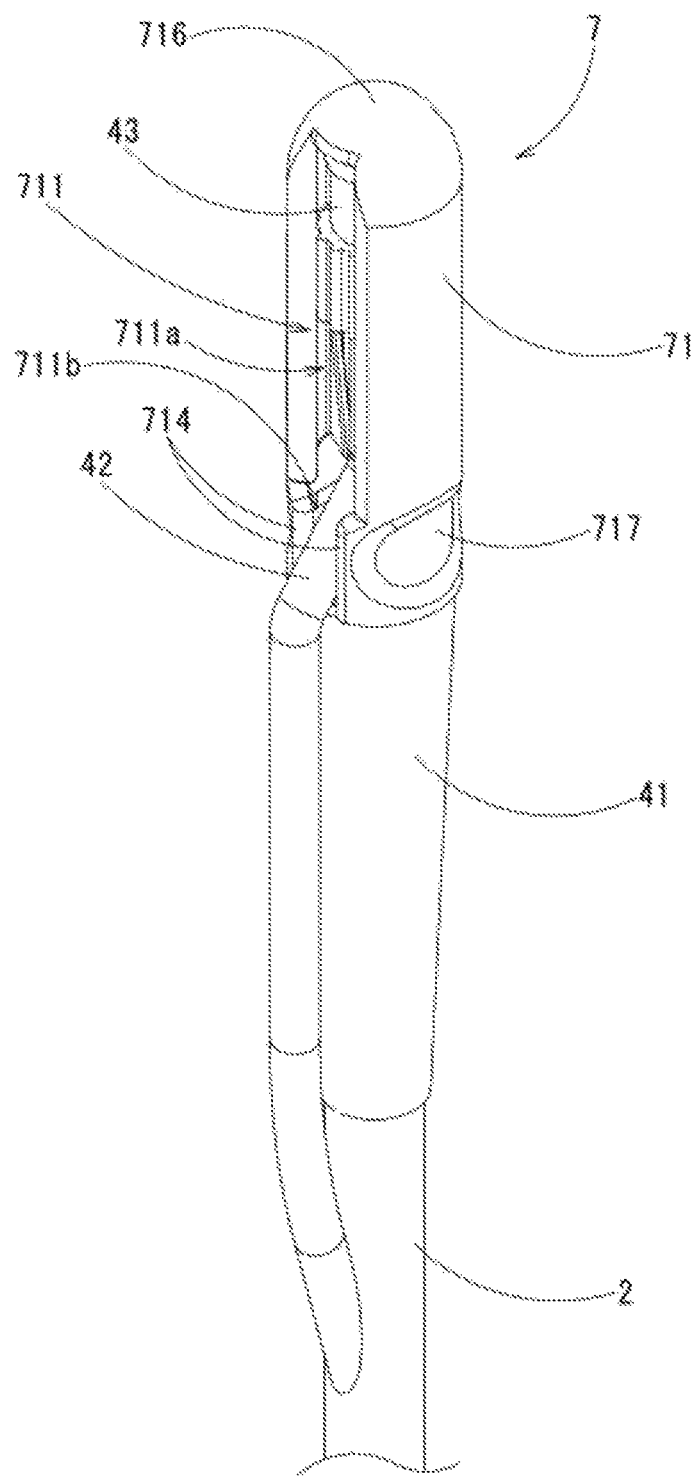
FIG. 7 is a perspective view illustrating a state where a water supply terminal is accommodated inside an accommodating portion according to the above-described embodiment.

In addition, the clamping portions 714 are a pair of wall portions located inside the water supply tube accommodating portion 711b on the distal end side (drain terminal 41 side) of the cap main body 71. A distance between the clamping portions 714 configured to include the pair of wall portions is set to be slightly smaller than the width of the water supply tube 42, and the distance increases outward. In addition, an inclined surface 715 having a downward slope toward the terminal accommodating portion 711a from the joint portion 72 side is formed between the clamping portions 714. In this manner, if the water supply terminal 43 is accommodated inside the terminal accommodating portion 711a, the water supply tube 42 is located on the clamping portions 714. If the water supply tube 42 is pressed toward the clamping portions 714, as illustrated in FIG. 7, the water supply tube 42 connected to the water supply terminal 43 is clamped on the distal end side of the cap main body 71 by the clamping portions 714. The water supply tube 42 is accommodated inside the water supply tube accommodating portion 711b along the inclined surface 715.

In addition, a proximal end portion 716 (end portion on a side opposite to the drain terminal 41) of the cap main body 71 is formed in a substantially semispherical shape. The diameter of the proximal end portion 716 is set to be larger than the diameter of the water supply terminal 43, and the projection 713 is disposed at the center of the proximal end portion 716. Accordingly, when the water supply terminal 43 is accommodated inside the accommodating portion 711, the water supply terminal 43 does not protrude outward of the cap main body 71. In addition, a pair of recess portions 717 is formed on the distal end side of the cap main body 71 in a direction orthogonal to the clamping portion 714. The recess portions 717 serve as a finger holding portion when a user operates the stylet unit 5.

Method of Accommodating Water Supply Terminal Inside Accommodating Portion]

In the balloon unit 1 as described above, a portion of the water supply tube 42 and the water supply terminal 43 are accommodated in the accommodating portion 711 of the cap 7 as follows, for example. First, the joint portion 72 of the cap 7 is mounted on the opening 411 of the drain terminal 41. Then, the opening 431 of the water supply terminal 43 is fitted to the projection 713 inside the accommodation portion 711 (inside the terminal accommodating portion 711a) of the cap main body 71, and the water supply terminal 43 is pressed into the terminal accommodating portion 711a. Thereafter, if the water supply tube 42 is pressed toward the clamping portions 714, the proximal end portion of the water supply tube 42 is clamped by the clamping portions 714, and is held inside the water supply tube accommodating portion 711b. In this manner, the water supply terminal 43 and the portion of the water supply tube 42 are accommodated inside the accommodating portion 711 as illustrated in FIG. 7.

[Method of Using Balloon Unit]

Figure 8:
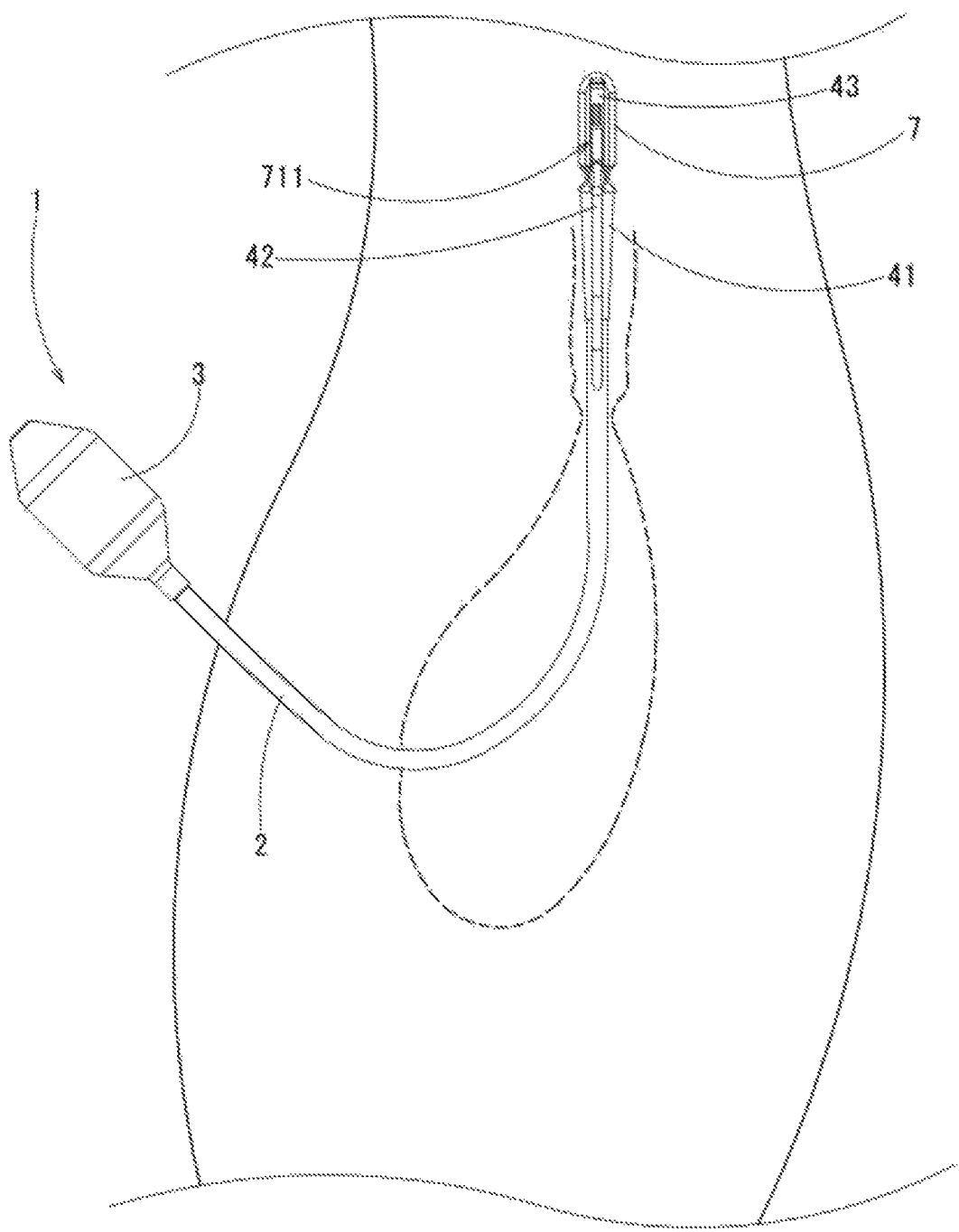
FIG. 8 is a schematic view illustrating a state where the uterine hemostatic balloon unit is inserted into a mother's body from an incised portion of the mother's body according to the above-described embodiment.

As illustrated in FIG. 8, for example, the balloon unit 1 as described above is inserted into a mother's body from an incised portion of a patient subjected to caesarean section. First, the balloon unit 1 in a state where the water supply terminal 43 is accommodated inside the accommodating portion 711 of the cap 7 is inserted into the uterus. At this time, the tube 2 of the balloon unit 1 needs to be greatly bent as illustrated in FIG. 8. Then, the connector 4 is pulled out from the body of the patient through the vagina, and the hemostatic balloon 3 is located inside the uterus.

According to the present embodiment, the stylet 6 is formed of pure aluminum. Accordingly, the stylet 6 can maintain a shape thereof at a bent angle, and is deformed when a strong force is applied thereto. Therefore, operability of the uterine hemostatic balloon unit 1 can be improved.

In addition, a method of inserting the balloon unit 1 into the mother's body from the incised portion has been described. However, as a matter of course, the balloon unit 1 can be properly used according to a usual method (inserting method from the vagina).

According to the present embodiment, the accommodating portion 711 is formed so that the water supply terminal 43 can be accommodated along the length direction of the drain terminal 41. Accordingly, if the water supply terminal 43 is accommodated in the accommodating portion 711, in a case where the balloon unit 1 is viewed from the connector 4 side, the cap 7 (cap main body 71) and the water supply terminal 43 are in an overlapped state. That is, the diameter of the connector 4 can be reduced, compared to a case where the drain terminal 41 and the water supply terminal 43 are arrayed in the direction orthogonal to the length direction of the drain terminal 41. Accordingly, when the cap 7 is inserted from the incised portion of the patient subjected to caesarean section, insertion resistance can be reduced. Therefore, it is possible to prevent damage to a birth canal which is likely to be damaged when the balloon unit 1 is inserted from the incised portion of the patient subjected to the caesarean section. In addition, when the water supply terminal 43 is accommodated in the accommodating portion 711, the movement of the water supply terminal 43 in the above-described direction is regulated by the stopper portion (projection 713 and clamping portions 714). While the cap 7 is inserted, it is possible to prevent the insertion resistance from increasing due to the water supply terminal 43 detached from the accommodating portion 711.

The present invention is not limited to the above-described embodiment, and various modifications can be added thereto within the scope not departing from the gist of the present invention. For example, in the above-described embodiment, an example has been described in which the projection 713 and the clamping portions 714 are used as the stopper portion. However, the present invention is not limited thereto. For example, projections extending toward side portions facing each other may be respectively disposed on both side portions of a substantially central portion of the accommodating portion 711, and the water supply terminal 43 may be held by the projections. That is, a shape of the stopper portion can be appropriately changed.

In the above-described embodiment, the accommodating portion 711 is configured to include the through-hole. However, the present invention is not limited thereto. For example, one of the surfaces may be closed. In addition, in the above-described embodiment, the stylet 6 is formed of the pure aluminum. However, without being limited thereto, for example, the stylet 6 may be formed of an aluminum alloy. That is, a composition thereof may be optionally selected as long as the stylet 6 can maintain the shape of the tube 2 and is deformed when the strong force is applied thereto.

In the above-described embodiment, the stylet 6 is accommodated inside the drain terminal 41. However, the present invention is not limited thereto. For example, a hole portion into which the stylet can be inserted may be formed in the tube 2 so that the stylet 6 can be accommodated inside the hole portion.

In the above-described embodiment, the water supply terminal 43 is connected to the two-way cock 44. However, the present invention is not limited thereto. For example, a one-way valve or a high-speed injection valve may be connected to the water supply terminal 43. Out of these, in a case of the one-way valve, a cock does not have to be turned off when a syringe is replaced during water supply. If the syringe is detached, the valve is opened, thereby preventing a reverse flow from the hemostatic balloon 3 side. In a case of the high-speed injection valve, two one-way valves are combined with each other. An infusion bag of distilled water or physiological saline solution is connected to an upper connection port. The water supply terminal 43 and the syringe are connected to each other. If the syringe is pulled, the valve on the infusion bag side is opened, and the valve on the water supply terminal 43 side is closed, thereby causing the water to flow into the syringe. On the other hand, if the syringe is pressed, the valve on the infusion bag side is closed, and the valve on the water supply terminal 43 side is opened, thereby causing the water to flow into the hemostatic balloon 3. Therefore, the water can be repeatedly injected into the hemostatic balloon 3 without detaching the valve or the syringe.

INDUSTRIAL APPLICABILITY

It is possible to provide a uterine hemostatic balloon unit of preventing bleeding inside a uterus.

What is claimed is:
1. A uterine hemostatic balloon unit comprising:
a flexible tube;
a hemostatic balloon disposed in a distal end portion of the flexible tube;
a connector disposed in the flexible tube, and
a cap to be detachably attached to a proximal end portion of the flexible tube,
wherein the flexible tube has
a drain channel for draining uterine blood outward by being open on a distal end side from the hemostatic balloon, and
a water supply channel communicating with the hemostatic balloon, wherein the connector has
a drain terminal communicating with the drain channel and disposed in a proximal end portion of the flexible tube,
a flexible water supply tube communicating with the water supply channel on a distal end side from the drain terminal and extending by being bifurcated outward of the flexible tube, and
a water supply terminal disposed in a proximal end of the water supply tube and communicating with the water supply tube,
wherein the cap detachably fits to an opening of the drain terminal and has an accommodating portion capable of accommodating at least a portion of the water supply terminal along a length direction of the drain terminal, and the accommodating portion is open in a direction orthogonal to the length direction of the drain terminal, and
wherein the accommodating portion has a stopper portion which regulates movement of the water supply terminal in the direction orthogonal to the length direction of the drain terminal, and the stopper portion has a clamping portion which clamps the water supply tube on the drain terminal side in the accommodating portion, when the water supply terminal is accommodated inside the accommodating portion.

2. The uterine hemostatic balloon unit according to claim 1, wherein the stopper portion further has a projection which projects from a surface on a side opposite to the drain terminal side in the accommodating portion so as to be fitted into an opening of the water supply terminal, when the water supply terminal is accommodated inside the accommodating portion.

3. The uterine hemostatic balloon unit according to claim 2, further comprising:
a stylet fixed to a distal end side of the cap and holding a shape of the flexible tube when the stylet is inserted into the flexible tube,
wherein when the cap is mounted on the opening of the drain terminal, a distal end of the stylet is located in a portion from a proximal end portion of the hemostatic balloon to a center of the hemostatic balloon.

4. The uterine hemostatic balloon unit a.ccording to claim 2, wherein a metal wire rod is enclosed on a distal end side of the water supply tube.

5. The uterine hemostatic balloon unit according to claim 1, wherein the accommodating portion is configured to include a through-hole penetrating the cap.

6. The uterine hemostatic balloon unit according to claim 5, further comprising:
a stylet fixed to a distal end side of the cap and holding a shape of the flexible tube when the stylet is inserted into the flexible tube.

wherein when the cap is mounted on the opening of the drain terminal, a distal end of the stylet is located in a portion from a proximal end portion of the hemostatic balloon to a center of the hemostatic balloon.

7. The uterine hemostatic balloon unit according to claim 1, further comprising:
a stylet fixed to a distal end side of the cap and holding a shape of the flexible tube when the stylet is inserted into the flexible tube,
wherein when the cap is mounted on the opening of the drain terminal, a distal end of the stylet is located in a portion from a proximal end portion of the hemostatic balloon to a center of the hemostatic balloon.

8. The uterine hemostatic balloon unit according to claim 7, wherein a metal wire rod is enclosed on a distal end side of the water supply tube.

9. The uterine hemostatic balloon unit according to claim 1, wherein a metal wire rod is enclosed on a distal end side of the water supply tube.

10. A uterine hemostatic balloon unit comprising:
a flexible tube;
a hemostatic balloon disposed in a distal end portion of the flexible tube;
a connector disposed in the flexible tube; and
a cap to be detachably attached to a proximal end portion of the flexible tube,
wherein the flexible tube has
a drain channel for draining uterine blood outward by being open on a distal end side from the hemostatic balloon, and
a water supply channel communicating with the hemostatic balloon, wherein the connector has
a drain terminal communicating with the drain channel and disposed in a proximal end portion of the flexible tube,
a flexible water supply tube communicating with the water supply channel on a distal end side from the drain terminal and extending by being bifurcated outward of the flexible tube, and
a water supply terminal disposed in a proximal end of the water supply tube and communicating with the water supply tube,
wherein the cap detachably fits to an opening of the drain terminal and has an accommodating portion capable of accommodating at least a portion of the water supply terminal along a length direction of the drain terminal, and the accommodating portion is open in a direction orthogonal to the length direction of the drain terminal, and
wherein the accommodating portion has a stopper portion which regulates movement of the water supply terminal in the direction orthogonal to the length direction of the drain terminal, and the stopper portion has a projection which projects from a surface on a side opposite to the drain terminal side in the accommodating portion so as to be fitted into an opening of the water supply terminal, when the water supply terminal is accommodated inside the accommodating portion.

11. The uterine hemostatic balloon unit according to claim 10, wherein the accommodating portion is configured to include a through-hole penetrating the cap.

12. The uterine hemostatic balloon unit according to claim 11, further comprising:
a stylet fixed to a distal end side of the cap and holding a shape of the flexible tube when the stylet is inserted into the flexible tube,
wherein when the cap is mounted on the opening of the drain terminal, a distil end of the stylet is located in a portion from a proximal end portion of the hemostatic balloon to a center of the hemostatic balloon.

13. The uterine hemostatic balloon unit according to claim 10, further comprising:
a stylet fixed to a distal end side of the cap and holding a shape of the flexible tube when the stylet is inserted into the flexible tube,
wherein when the cap is mounted on the opening of the drain terminal, a distal end of the stylet is located in a portion from a proximal end portion of the hemostatic balloon to a center of the hemostatic balloon.

14. The uterine hemostatic balloon unit according to claim 10, wherein a metal wire rod is enclosed on a distal end side of the water supply tube.

15. A uterine hemostatic balloon unit comprising:
a flexible;
a hemostatic balloon disposed in a distal end portion of the flexible tube
a connector disposed in the flexible tube; and
a cap to be detachably attached to a proximal end portion of the flexible tube, wherein the flexible tube has
a drain channel for draining uterine blood outward by being open on a distal end side from the hemostatic balloon, and
a water supply channel communicating with the hemostatic balloon, wherein the connector has
a drain terminal communicating with the drain channel and disposed in a proximal end portion of the flexible tube,
a flexible water supply tube communicating with the water supply channel on a distal end side from the drain terminal and extending by being bifurcated outward of the flexible tube, and,
a water supply terminal disposed in a proximal end of the water supply tube and communicating with the water supply tube
wherein the cap detachably fits to an opening of the drain terminal and has an accommodating portion capable of accommodating at least a portion of the water supply terminal along a length direction of the drain terminal, and the accommodating portion is open in a direction orthogonal to the length direction of the drain terminal,
the uterine hemostatic balloon unit further comprising a stylet fixed to a distal end side of the cap and holding a shape of the flexible tube when the stylet is inserted into the flexible tube, wherein when the cap is mounted on the opening of the drain terminal, a distal end of the stylet is located in a portion from a proximal end portion of the hemostatic balloon to a center of the hemostatic balloon.

16. The uterine hemostatic balloon unit according to claim 15, wherein the stylet is formed of pure aluminum.

17. The uterine hemostatic balloon unit according to claim 15, wherein a metal wire rod is enclosed on a distal end side of the water supply tube.

18. The uterine hemostatic balloon unit according to claim 15, wherein the accommodating portion is configured to include a through-hole penetrating the cap.

19. A uterine hemostatic balloon unit comprising:
a flexible tube;
a hemostatic balloon disposed in a. distal end portion of the flexible tube;
a connector disposed in the flexible tube; and
a cap to be detachably attached to a proximal end of the flexible tube, wherein the flexible tube has a drain channel for draining uterine blood outward by being open on a distal end side from the hemostatic balloon, and a water supply channel communicating with the hemostatic balloon, wherein the connector has a drain terminal communicating with the drain channel and disposed in a proximal end portion of the flexible tube, a flexible water supply tube communicating with the water supply channel on a distal end side from the drain terminal and extending by being bifurcated outward of the flexible tube, and a water supply terminal disposed in a proximal end of the water supply tube and communicating with the water supply tube, wherein the cap detachably fits to an opening of the drain terminal and has an accommodating portion capable of accommodating at least a portion of the water supply terminal along a length direction of the drain terminal and the accommodating portion is open in a direction orthogonal to the length direction of the drain terminal, and wherein a metal wire rod is enclosed on a distal end side of the water supply tube.

20. The uterine hemostatic balloon unit according to claim 19, wherein the accommodating portion is configured to include a through-hole penetrating the cap.

\* \* \* \* \*

UNITED STATES PATENT AND TRADEMARK OFFICE
CERTIFICATE OF CORRECTION

PATENT NO. : 11,141,194 B2  
APPLICATION NO. : 16/439001  
DATED : October 12, 2021  
INVENTOR(S) : Wakabayashi et al.

Page 1 of 1

It is certified that error appears in the above-identified patent and that said Letters Patent is hereby corrected as shown below:

In the Claims

Column 10, Claim 4, Line 57, please delete "a.ccording" and replace with -- according --; and Column 12, Claim 15, Line 18, please insert -- tube -- after "flexible.".

Signed and Sealed this  
Twenty-second Day of February, 2022

Drew Hirshfeld  
*Performing the Functions and Duties of the*  
*Under Secretary of Commerce for Intellectual Property and*  
*Director of the United States Patent and Trademark Office*